United States Patent [19]

Meek et al.

[11] Plant 4,526

[45] Apr. 29, 1980

[54] CHRYSANTHEMUM PLANT

[75] Inventors: Jack M. Meek; William E. Duffett, both of Salinas, Calif.

[73] Assignee: Grace M. Mack, New Canaan, Conn.

[21] Appl. No.: 962,847

[22] Filed: Nov. 22, 1978

[51] Int. Cl.[2] ..... A01H 5/00

[52] U.S. Cl. ..... Plt./75

[58] Field of Search ..... Plt./78, 75

*Primary Examiner*—Robert E. Bagwill

*Attorney, Agent, or Firm*—Donald D. Jeffery

[57] ABSTRACT

A chrysanthemum cultivar which is a sport of the cultivar Patriot, U.S. Plant Pat. No. 3,897, Compatriot being distinguished from Patriot by its medium yellow ray floret color.

1 Drawing Figure

The present invention comprises a new and distinct cultivar of *Chrysanthemum morifolium,* Ramat., hereinafter referred to by the cultivar name Compatriot.

Compatriot is a spontaneous yellow mutant of the cultivar Patriot, disclosed in U.S. Plant Pat. No. 3,897.

Compatriot was discovered and selected as one branch of a plant within a flowering block of Patriot by Jack M. Meek on Oct. 4, 1976. The first act of asexual reproduction of Compatriot was accomplished when vegetative cuttings were taken from the initial selection in March, 1977, by a technician working under the formulations established and supervised by Jack M. Meek and William E. Duffett. Horticultural examination of selected units initiated June 20, 1977 has demonstrated that the combination of characteristics as herein disclosed for Compatriot are firmly fixed and are retained through successive generations of asexual reproduction.

Compatriot has not been observed under all possible environmental conditions. The phenotype may vary significantly with variations in environment such as temperature, light intensity, and daylength. The following observations, measurements, and comparisons describe plants grown in a field in Salinas, Calif. under conditions which are generally described in *Local Climatological Data, Annual Summary with Comparative Data, Salinas, Calif.,* 1977 *and* 1978, U.S. Department of Commerce, National Oceanic and Atmospheric Administration, Environmental Data Service, Washington, D.C.

The following traits have been repeatedly observed and are determined to be basic characteristics of Compatriot which in combination distinguish this chrysanthemum as a new and distinct cultivar:

(1) Flat capitulum form.

(2) Decorative capitulum type (commercial double).

(3) Medium yellow ray floret color.

(4) Diameter across face of capitulum up to 60 mm.

(5) Short plant height (averaging 25 cm. to 30 cm. under an outdoor natural season environment from a July 10 plant of a rooted cutting in Salinas, Calif.

(6) Average natural season flowering date of September 10 (California).

(7) Average flowering response period of 7 weeks in photoperiodic controlled flowering programs.

The accompanying photographic drawing shows typical inflorescence and foliage characteristics of Compatriot. Some difficulty was encountered in obtaining accurate color representation, with the color of inflorescence of Compatriot in the photograph being more golden, or less yellow than the actual flower color of Compatriot. The color readings within the following description are, however, correct.

Of the many commercially available cultivars known to the present inventors, the most similar existing cultivar in comparison to Compatriot is Patriot.

Reference is made to attached Chart A which compares certain characteristics of Compatriot with the same characteristics of Patriot. It will be noted that in comparison to Patriot, Compatriot has different ray floret color and greater range of diameter across face of capitulum. The capitulum form, capitulum type, average natural season flower date, plant height, and branching pattern of Compatriot are similar to those same characteristics of Patriot.

In the following description, color references are made to A Limit Color Cascade, The Munsel Company, 1972 edition. The color values were determined between 11:00 and 11:30 A.M. on Sept. 12, 1978 under 100 foot-candle light intensity and between 2:30 and 3:00 P.M. on June 27, 1979 under 200 foot-candle light intensity at Salinas, Calif.

Botanical classification: *Chrysanthemum morifolium,* Ramat., cv. Compatriot

I. INFLORESCENCE:

A. *Capitulum.*—Form: flat. Type: decorative. Permanence: 14–21 days. Diameter across face: 45 to 60 mm.

B. *Corolla of ray florets.*—Color (abaxial): 25–6 to 26–5, oxidizing rapidly to 25–4 to 26–3. Color (adaxial): 25–3 to 25–2. Color (General Tonality at a Distance of 3 Feet): medium yellow 25–6 to 26–5, oxidizing rapidly to light yellow 25–4 to 26–3.

C. *Reproductive organs.*—Androecium: present disc florets; scant pollen. Gynoecium: present both ray and disc florets.

II. PLANT:

A. *General appearance.*—Short height, semi-spreading branching pattern.

B. *Foliage.*—Color (abaxial): 20–13 to 20–14. Color (adaxial): 20–13 overlaid with white.

CHART A

COMPARISON OF COMPATRIOT AND PATRIOT.

| Cultivar | Ray Floret Color | Capitulm Form And Type | Average Natural Season Flower Date | Plant Height | Branching Pattern And Spread | Diameter Across Face Of Capitulum |
|---|---|---|---|---|---|---|
| Compatriot | Medium yellow | Flat decorative | September 10 | Short from 25 to 30 cm. | Semi-spreading up to 25 cm. | 45 to 60 mm. |
| Patriot | Ivory white | Flat decorative | September 10 | Short, from 25 to 30 cm. | Semi-spreading up to 25 cm. | 50 to 60 mm. |

-continued

CHART A

COMPARISON OF COMPATRIOT AND PATRIOT.

| Cultivar | Ray Floret Color | Capitulm Form And Type | Average Natural Season Flower Date | Plant Height | Branching Pattern And Spread | Diameter Across Face Of Capitulum |
|---|---|---|---|---|---|---|
| | | | | | to 25 cm. | |

COMPARISONS MADE OF PLANTS GROWN UNDER NATURAL SEASON OUTDOOR FIELD CONDITIONS IN SALINAS, CALIFORNIA.

We claim:

1. A new and distinct cultivar of *Chrysanthemum morifolium,* Ramat., plant known by the name of Compatriot and particularly characterized as to uniqueness by the combined characteristics of flat capitulum form, decorative capitulum type, medium yellow ray floret color, diameter across face of capitulum up to 60 mm., short plant height, semi-spreading branching pattern, average natural season flowering date of September 10, and average flowering response period of seven weeks in photoperiodic controlled short day program.

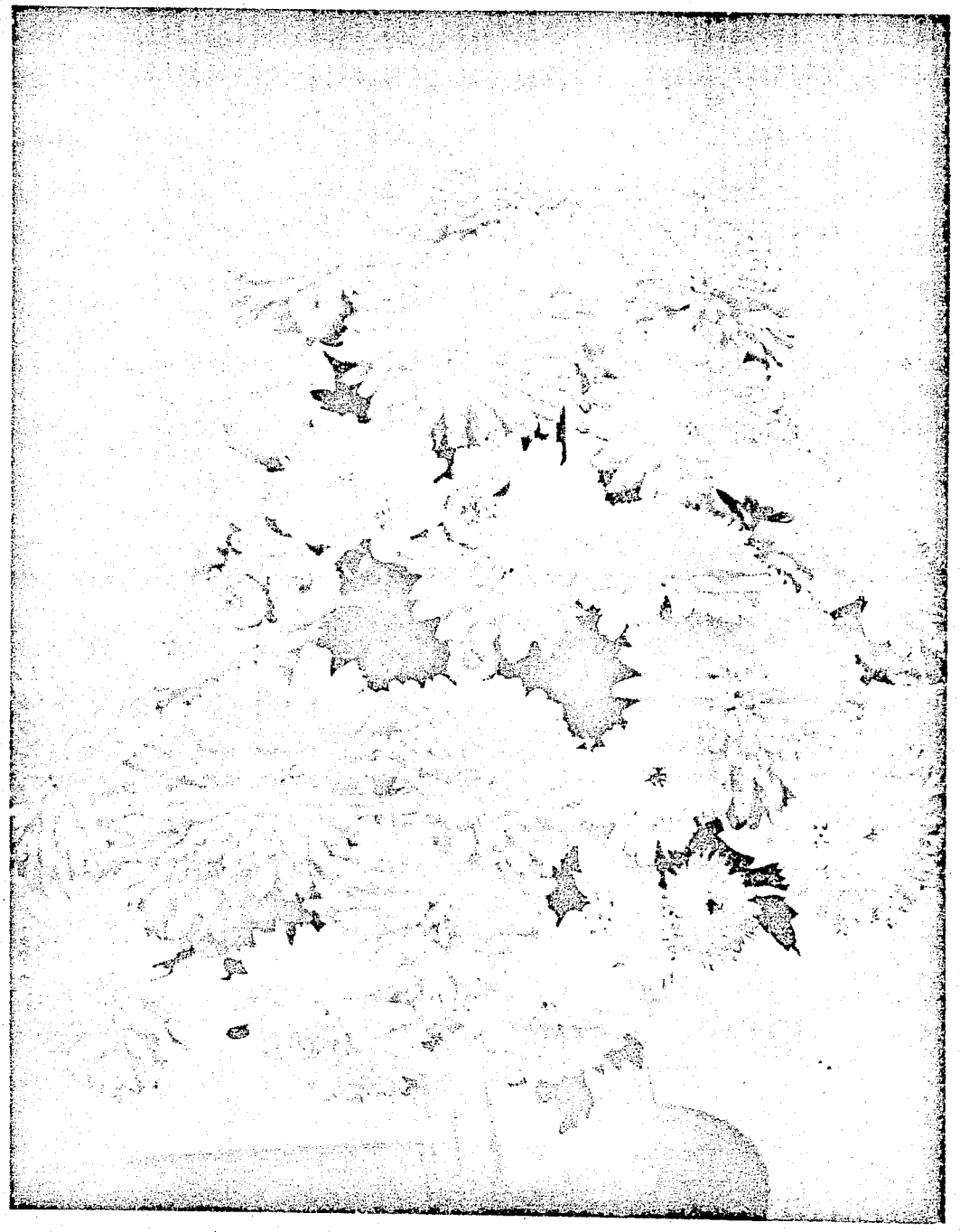

* * * * *